US00PP32504P2

(12) United States Plant Patent
Graff

(10) Patent No.: US PP32,504 P2
(45) Date of Patent: Nov. 24, 2020

(54) ***MANDEVILLA* PLANT NAMED 'QD2'**

(50) Latin Name: *Mandevilla sanderi*
Varietal Denomination: QD2

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 16/873,004

(22) Filed: Jan. 14, 2020

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. A. Whealy

(57) ABSTRACT

A new and distinct cultivar of *Mandevilla* plant named 'QD2', characterized by its compact, broadly upright to vining plant habit; moderately vigorous to vigorous growth habit; freely branching habit; dense and bushy appearance; dark green-colored leaves; freely flowering habit; and relatively large white-colored flowers with greyed orange-colored throats.

2 Drawing Sheets

Figure 1:
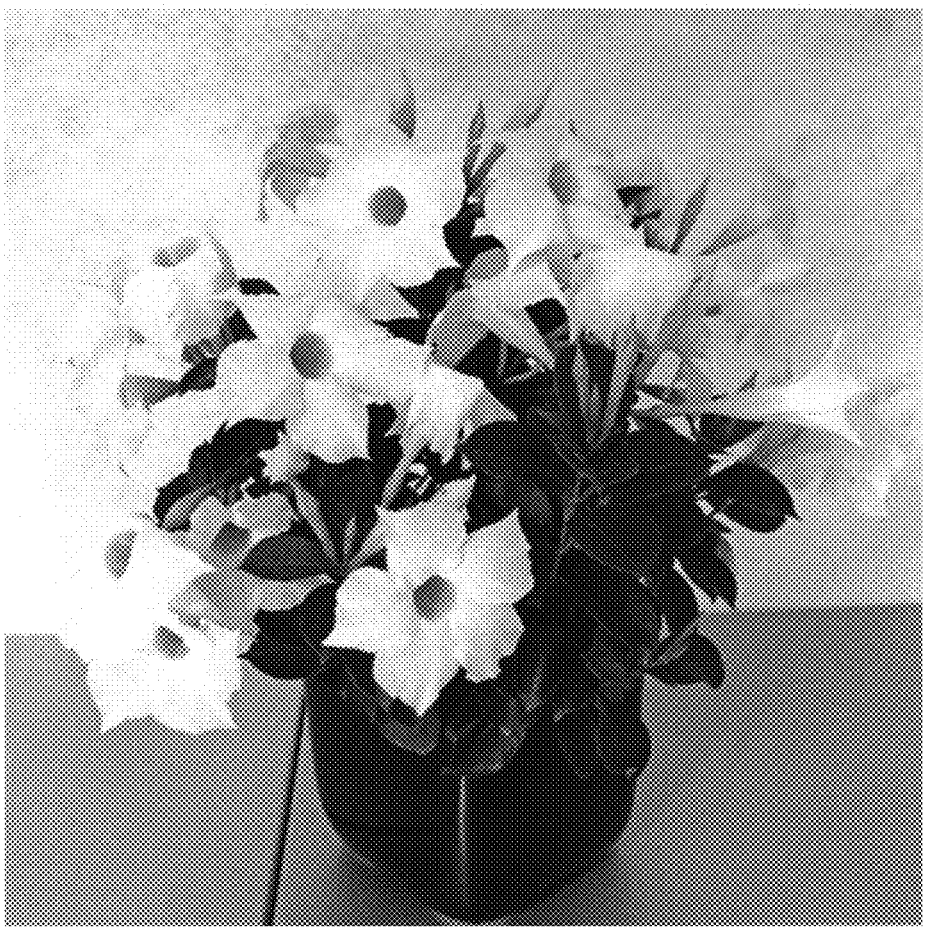

Botanical designation: *Mandevilla sanderi.*
Cultivar denomination: 'QD2'.

BACKGROUND OF THE INVENTION

The present invention relates to a new and distinct cultivar of *Mandevilla* plant, botanically known as *Mandevilla sanderi* and hereinafter referred to by the name 'QD2'.

The new *Mandevilla* plant is a product of a planned breeding program conducted by the Inventor in Sabro, Denmark. The objective of the breeding program is to create new compact and freely branching *Mandevilla* plants with numerous attractive flowers.

The new *Mandevilla* plant originated from a cross-pollination conducted by the Inventor in Sabro, Denmark in August, 2015 of a proprietary selection of *Mandevilla sanderi* identified as code number 2011-0010, not patented, as the female, or seed, parent with a proprietary selection of *Mandevilla sanderi* identified as code number 2011-0011, not patented, as the male, or pollen, parent. The new *Mandevilla* plant was discovered and selected by the Inventor as a single flowering plant from within the progeny of the stated cross-pollination in a controlled greenhouse environment in Sabro, Denmark in May, 2016.

Asexual reproduction of the new *Mandevilla* plant by cuttings in a controlled greenhouse environment in Sabro, Denmark, since September, 2016 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'QD2'. These characteristics in combination distinguish 'QD2' as a new and distinct *Mandevilla* plant:

1. Compact, broadly upright to vining plant habit.
2. Moderately vigorous to vigorous growth habit.
3. Freely branching habit; dense and bushy appearance.
4. Dark green-colored leaves.
5. Freely flowering habit.
6. Relatively large white-colored flowers with greyed orange-colored throats.

Plants of the new *Mandevilla* can be compared to plants of the female parent selection. Plants of the new *Mandevilla* differ primarily from plants of the female parent selection in flower color as plants of the new *Mandevilla* have white-colored flowers whereas plants of the female parent selection have light pink-colored flowers.

Plants of the new *Mandevilla* can be compared to plants of the male parent selection. Plants of the new *Mandevilla* differ primarily from plants of the male parent selection in growth habit as plants of the new *Mandevilla* are more compact and denser than and not as vigorous and open as plants of the male parent selection.

Plants of the new *Mandevilla* can also be compared to plants of *Mandevilla sanderi* 'Sundaville White', not patented. In side-by-side comparisons, plants of the new *Mandevilla* differ primarily from plants 'Sundaville White' in the following characteristics:

1. Plants of the new *Mandevilla* are more compact than and not as vigorous as plants of 'Sundaville White'.
2. Plants of the new *Mandevilla* do not produce tendrils whereas plants of 'Sundaville White' produce tendrils.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1 of 2) comprises a side perspective view of a typical flowering plant of 'QD2' grown in a container.

Figure 2:
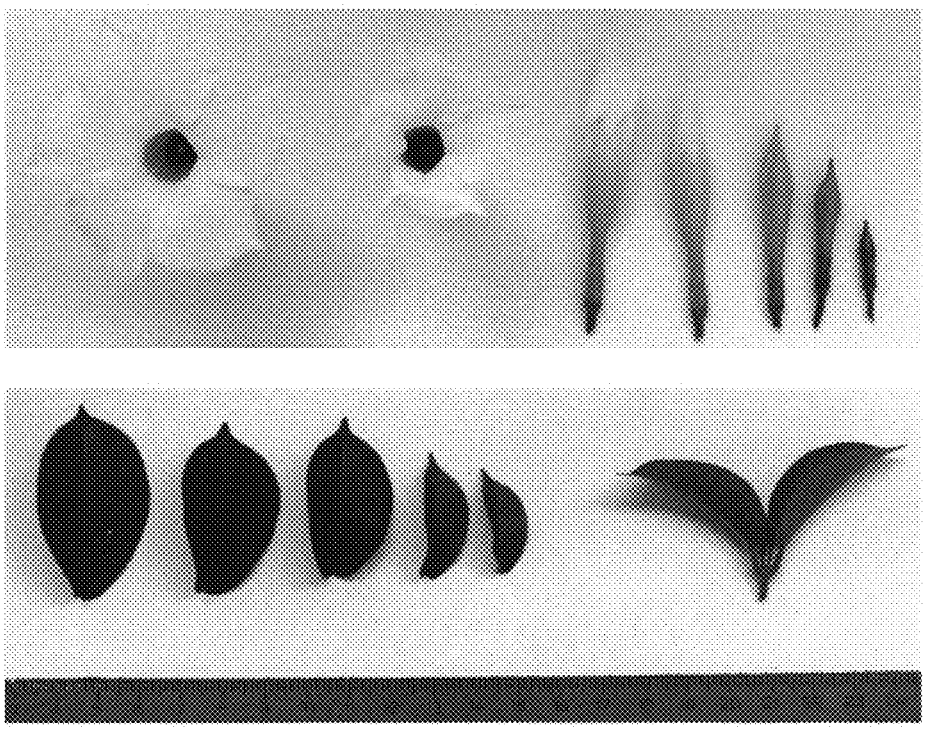

The photographs on the second sheet (FIG. 2 of 2) are close-up views of typical developing flowers and developing leaves of 'QD2'.

DETAILED BOTANICAL DESCRIPTION

The aforementioned photographs and following observations, measurements and values describe plants grown during the autumn in 13-cm containers in a glass-covered greenhouse in Sabro, Denmark and under cultural practices typical of commercial *Mandevilla* production. During the production of the plants, day temperatures ranged from 20° C. to 25° C., night temperatures ranged from 19° C. to 21° C. and light levels ranged from 40 klux to 50 klux. Plants were pinched two times and were 30 weeks old when the photographs and description were taken. In the following description, color references are made to The Royal Horticultural Society Colour Chart, 2001 Edition, except where general terms of ordinary dictionary significance are used.

Botanical classification: *Mandevilla sanderi* 'QD2'.

Parentage:

*Female, or seed, parent*.—Proprietary selection of *Mandevilla sanderi* identified as code number 2011-0010, not patented.

*Male, or pollen, parent*.—Proprietary selection of *Mandevilla sanderi* identified as code number 2011-0011, not patented.

Propagation:

*Type*.—By vegetative cuttings.

*Time to initiate roots, summer*.—About three weeks at soil and ambient temperatures about 21° C.

*Time to initiate roots, winter*.—About four weeks at soil and ambient temperatures about 21° C.

*Time to produce a rooted young plant, summer*.—About seven weeks at soil and ambient temperatures about 21° C.

*Time to produce a rooted young plant, winter*.—About eight weeks at soil and ambient temperatures about 21° C.

*Root description*.—Fine, fleshy; typically close to 161C in color, actual color of the roots is dependent on substrate composition, water quality, fertilizers, substrate temperature and physiological age of roots.

*Rooting habit*.—Freely branching; dense.

Plant description:

*Plant and growth habit*.—Compact, broadly upright to vining plant habit; overall plant shape is broadly obovate; moderately vigorous to vigorous growth habit and moderate growth rate; freely branching habit; dense and bushy appearance.

*Plant height, soil level to top of foliar plane*.—About 25 cm to 35 cm.

*Plant height, soil level to top of floral plane*.—About 28 cm to 38 cm.

*Plant diameter* (*spread*).—About 25 cm to 35 cm.

*Lateral branch description*.—Branching habit: Freely branching habit, about four to six primary lateral branches each with typically four to eight secondary lateral branches developing per plant. Length: About 10 cm to 25 cm. Diameter: About 5 mm. Internode length: About 2 cm to 4 cm. Aspect: Mostly upright to vining. Strength: Strong. Texture and luster: Smooth, glabrous; semi-glossy to matte. Color, developing: Close to 144A. Color, developed: Close to 146A; becoming closer to 152A with subsequent development.

Leaf description:

*Arrangement*.—Opposite, simple.

*Length*.—About 4 cm to 6 cm.

*Width*.—About 2 cm to 6 cm.

*Shape*.—Elliptic to oblong.

*Apex*.—Cuspidate to mucronate.

*Base*.—Obtuse to rounded cordate.

*Margin*.—Entire, slightly undulate.

*Texture and luster, upper surface*.—Smooth, glabrous; not rugose; slightly coriaceous; semi-glossy.

*Texture and luster, lower surface*.—Smooth, glabrous; not rugose; slightly coriaceous; matte.

*Venation pattern*.—Pinnate.

*Color*.—Developing leaves, upper surface: Close to 137A. Developing leaves, lower surface: Close to 138B. Full expanded leaves, upper surface: Close to 136A; venation, close to 137C. Fully expanded leaves, lower surface: Close to 138A; venation, close to 135A.

*Petioles*.—Length: About 5 mm to 10 mm. Diameter: About 2 mm to 3 mm. Strength: Moderately strong to strong. Texture and luster, upper and lower surfaces: Smooth, glabrous; slightly glossy to matte. Color, upper surface: Close to 143A. Color, lower surface: Close to 143C.

Flower description:

*Flower type and flowering habit*.—Single salverform flowers arranged singly or in terminal or axillary cymes; flowers star-shaped and face upright to outwardly; freely flowering habit with about three to four flower buds and about one to two open flowers per inflorescence.

*Natural flowering season*.—Plants flower continuously from spring into the autumn in Denmark; plants begin flowering about nine to twelve weeks after final pinch.

*Flower longevity on the plant*.—About 8 to 14 days; flowers persistent.

*Fragrance*.—None detected.

*Inflorescence height* (*before flowers open*).—About 3 cm to 5 cm.

*Inflorescence diameter* (*before flowers open*).—About 5 cm to 7 cm.

*Flower buds*.—Length: About 2 cm to 7 cm. Diameter: About 1 cm to 1.5 cm. Shape: Rhomboidal. Texture and luster: Smooth, glabrous; slightly glossy. Color: Close to 150C.

*Flowers*.—Appearance: Flared trumpet, petals fused and five-parted; petals imbricate. Diameter: About 8 cm to 11 cm. Depth (length): About 4 cm to 5 cm. Throat diameter: About 2 cm to 3 cm. Tube length: About 1.5 cm to 2.5 cm. Tube diameter: About 4 mm to 6 mm.

*Petals*.—Quantity and arrangement: Five petals arranged in a single whorl; proximally, petals are fused into a funnelform tube. Petal length: About 3 cm to 5 cm. Petal width: About 3 cm to 5 cm. Petal shape and appearance: Unequal spatulate. Petal apex: Acuminate to mucronate. Petal margin: Entire; slightly undulate. Petal texture and luster, upper surface: Smooth, glabrous; not rugose; moderately velvety; matte. Petal texture and luster, lower surface: Smooth, glabrous; not rugose; moderately velvety; moderately glossy. Throat texture: Smooth, glabrous; moderately velvety. Tube texture: Smooth, glabrous; slightly velvety. Color: Petal, when opening, upper and lower surfaces: Close to 155D. Petal, fully opened, upper and lower surfaces: Close to 155D; venation, close to 155D; color does not change with development. Throat: Close to 163B; venation, close to 163B. Tube: Close to N144D; venation, close to N144D.

*Sepals*.—Quantity and arrangement: Five sepals arranged in a single whorl. Sepal length: About 7 mm to 12 mm. Sepal width: About 2 mm to 5 mm. Sepal shape: Lanceolate. Sepal apex: Acuminate. Sepal base: Rounded. Sepal margin: Entire. Sepal texture and luster, upper and lower surfaces: Smooth, glabrous; semi-glossy. Sepal color: When opening, upper and lower surfaces: Close to 145B; towards the apex, close to 46B; towards the base, close to 146B. Fully opened, upper and lower surfaces: Close to 145B; towards the apex, close to 46B; towards the base, close to 146B.

*Peduncles*.—Length: About 1 cm to 4 cm. Diameter: About 2 mm to 4 mm. Strength: Strong. Aspect: Mostly upright. Texture and luster: Smooth, glabrous; semi-glossy. Color: Close to 143A.

*Pedicels*.—Length: About 8 mm to 20 mm. Diameter: About 3 mm to 5 mm. Strength: Strong. Aspect: Mostly upright. Texture and luster: Smooth, glabrous; semi-glossy. Color: Close to 146C.

*Reproductive organs*.—Stamens: Quantity and arrangement: Typically five; basifixed; anthers connivent. Filament length: About 1 mm to 2 mm. Filament color: Close to 145D. Anther size: About 2 mm by 6 mm. Anther shape: Narrowly oblong. Anther color: Close to 162C. Pollen amount: Moderate. Pollen color: Close to 162C. Pistils: Quantity: Typically one or two. Pistil length: About 2 cm. Style length: About 5 mm to 20 mm. Style color: Close to 193B. Stigma diameter: About 3 mm to 4 mm. Stigma shape: Rounded to deltoid. Stigma color: Close to 138B. Ovary color: Close to 193A.

*Fruits*.—Quantity per flower: One. Length: About 1 cm to 2 cm. Diameter: About 2 mm to 5 mm. Texture: Smooth, glabrous. Color: Close to 138A.

*Seeds*.—Quantity per fruit: More than 100. Length: About 5 mm to 10 mm. Diameter: About 0.5 mm. Texture: Smooth, glabrous. Color: Close to 200D.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures of about 10° C. to 44° C. and to be suitable for USDA Hardiness Zones 10b through 13.

It is claimed:

1. A new and distinct *Mandevilla* plant named 'QD2' as illustrated and described.

* * * * *